United States Patent
Shukla et al.

(10) Patent No.: US 6,977,248 B1
(45) Date of Patent: Dec. 20, 2005

(54) PHARMACEUTICAL PREPARATIONS FOR THE INHIBITION OF HERPES SIMPLEX VIRUS 1 ENTRY

(75) Inventors: Deepak Shukla, Skokie, MA (US); Robert D. Rosenberg, Boston, MA (US); Patricia G. Spear, Chicago, IL (US)

(73) Assignee: Massachusetts Institute of Technology, Cambridge, MA (US)

( * ) Notice: Subject to any disclaimer, the term of this patent is extended or adjusted under 35 U.S.C. 154(b) by 15 days.

(21) Appl. No.: 10/069,280

(22) PCT Filed: Aug. 25, 2000

(86) PCT No.: PCT/US00/23288

§ 371 (c)(1),
(2), (4) Date: Jul. 24, 2002

(87) PCT Pub. No.: WO01/13910

PCT Pub. Date: Mar. 1, 2001

Related U.S. Application Data (60) Provisional application No. 60/175,347, filed on Jan. 10, 2000, and provisional application No. 60/150,743, filed on Aug. 25, 1999.

(51) Int. Cl.[7] .......................... A61K 31/727; C12Q 1/48
(52) U.S. Cl. .......................................... 514/56; 435/15
(58) Field of Search ............................................ 514/56

(56) References Cited

U.S. PATENT DOCUMENTS 4,465,666 A * 8/1984 Lukas et al. ................. 424/145

FOREIGN PATENT DOCUMENTS

| WO | WO 98/05341 | * 2/1998 |
| WO | WO 98/42754 | * 10/1998 |
| WO | WO 99/22005 | * 5/1999 |

OTHER PUBLICATIONS

Lindahl, U. et al "Evidence for a 3–O–sulfated D–glucosamine residue . . . " (1980) PNAS vol. 77, No. 11, pp. 6551–6555.*
Lycke, E. et al "Binding of herpes simplex virus to cellular heparan . . . " J. Gen. Virol. (1991) vol. 72, pp. 1131–1137.*

* cited by examiner

Primary Examiner—James O. Wilson
Assistant Examiner—Leigh C. Maier
(74) Attorney, Agent, or Firm—Pearl Cohen Zedek Latzer, LLP; Mark Cohen (57) ABSTRACT

Disclosed herein are polysaccharide preparations enriched in 3-OST-3 modified heparan sulfate. Also disclosed are methods of treating herpes simplex viral type-1 infection using the pharmaceutical preparations of the invention.

28 Claims, 2 Drawing Sheets

```
m3-OST-3B (  1)  MGQRLSGGRSCLDVPGRFLPQPPPPPPVRRKLALLFAMLCIWLYMFLYSCAGSCTAAPG
h3-OST-3B (  1)  ...........................................L............V......A......

m3-OST-3B ( 61)  LLLLLGSGSRATHAQPTLVTAPNETSPKMPFRAPPANSLAAGKDTVGAGSQEEQSPEAPD
h3-OST-3B ( 61)  ..........A.DP.A.A...DG.P.RL......TP..S..EMAE..A.P......V...

m3-OST-3B (121)  SPSPISSFFSGAGSKQLPQAIIGVKKGGTRALLEFLRVHPDVRAVGAEPHFFDRSYHKG
h3-OST-3B (121)  ................S......................K..................D...
h3-OST-3A (148)  .........................................D.................D...

m3-OST-3B (181)  LAWYRDLMPRTLKGQITMEKTPSYFVTREAPARISAMSKDTKLIVVVRDPVTRAISDYTQ
h3-OST-3B (181)  ..........................D..................................
h3-OST-3A (196)  ..........................D..................................

m3-OST-3B (241)  TLSKRPDIPSFESLTFNRSAGLIDTSWSAIQIGLYAKHLEPWLRHFPLGQMLFVSGERL
h3-OST-3B (241)  .....T......K..T...............I.......H......IR..........
h3-OST-3A (256)  .....T......K..T...............I.......H......IR..........

m3-OST-3B (301)  VSDPAGELRRVQDFLGLKRIITDKHFYENOTKGFPCLKKAEGSGKPHCLGKTKGRAHPTI
h3-OST-3B (301)  I......G.....................K...........SR..........T..E.
h3-OST-3A (316)  I......G.....................K...........SR..........T..E.

m3-OST-3B (361)  AREVLRQLRDFYRPFNRKFYQMTGRDFGWD-
h3-OST-3B (361)  D...V.R..E......L......H......-
h3-OST-3A (376)  D...V.R..E......L......H......G
```

PHARMACEUTICAL PREPARATIONS FOR THE INHIBITION OF HERPES SIMPLEX VIRUS 1 ENTRY

RELATED APPLICATIONS

This application is the national phase of International (PCT) Patent Application Serial No. PCT/US00/23288, filed Aug. 25, 2000, which claims priority to U.S. application Ser. No. 60/150,743, filed on Aug. 25, 1999 and U.S. Application No. 60/175,347, filed on Jan. 10, 2000, the disclosures of which are incorporated herein by reference.

GOVERNMENT LICENSE RIGHTS

The U.S. Government has a paid-up license in this invention and the right in limited circumstances to require the patent owner to license others on reasonable terms as provided for by the terms of grant numbers AI-31494 and AI-36293, awarded by the National Institutes of Health (NIH).

FIELD OF THE INVENTION

The present invention relates generally to the field of virology. In particular, the present invention relates to methods and pharmaceutical preparations for inhibiting viral penetration and entry of herpes simplex virus 1 into mammalian cells via heparan sulfate binding.

BACKGROUND OF THE INVENTION

Heparan sulfate (HS) is widely expressed in animal and human tissues and has diverse roles in development, differentiation, and homeostasis. HS and other glycosaminoglycans are unbranched polymers covalently attached to the protein cores of proteoglycans, which are ubiquitously expressed as integral membrane proteins, glycerol phosphatidyl inositol-linked membrane proteins, and proteins of the extracellular matrix. The HS polymer is assembled by sequential addition of D-glucuronic acid (GlcA) alternating with N-acetyl glucosamine (GlcNAc). The chains are then modified heterogeneously and in domains by de-acetylation and sulfation of glucosamine, epimerization of GlcA residues to iduronic acid (IdoA), and sulfation of hydroxyl groups. These modifications provide specific binding sites for a variety of proteins, including cell adhesion molecules, growth factors, chemokines, and factors regulating angiogenesis and blood coagulation. Protein binding to HS may serve to sequester the protein at a particular site or to activate the protein. For example, the binding of antithrombin to a specific pentasaccharide sequence in HS results in activation of its anticoagulant activity (reviewed by Lindahl et al., 1998; Rosenberg et al., 1997).

Herpes simplex viruses (HSV) are human herpesviruses of the neurotropic alpha herpesvirus subfamily. Infections with HSV type 1 (HSV-1) and HSV type 2 (HSV-2) are highly prevalent. The usual manifestations of disease are mucocutaneous lesions of the mouth, face, eyes, or genitalia. Both HSV-1 and HSV-2 establish latent infections in neurons of peripheral ganglia and may reactivate to cause recurrent lesions. Rarely, the virus spreads to the central nervous system to cause meningitis or encephalitis (reviewed by Spear, 1993).

A number of viruses, including the human herpesviruses of the neurotropic alpha herpesvirus subfamily, use sites on HS as receptors for binding to cells (Byrnes and Griffin, 1998; Chung et al., 1998; Compton et al., 1993; Jackson et al., 1996; Shieh et al., 1992; Summerford and Samulski, 1998). Viral entry may require interactions with other cell surface receptors as well (Geraghty et al., 1998; Montgomery et al., 1996; Summerford et al., 1999; Warner et al., 1998).

Infection involves (1) virus attachment to the cell surface membrane, followed by (2) virus penetration and entry into the cells. These two steps can be experimentally dissociated. In the case of HSV-1 and HSV-2, the virus binds to cells through interactions of cell surface HS with viral envelope glycoproteins gB and/or gC (reviewed by Spear, 1993). Certain cell types, such as swine testis or Chinese hamster ovary (CHO) cells, are resistant to viral entry, even though the viral binding to these cells appears normal. Following binding, a third viral envelope glycoprotein, gD, interacts with one of multiple specific receptors, resulting in viral entry by fusion of the virion envelope with the target cell membrane. This fusion reaction requires the concerted action of three additional viral glycoproteins, gB, gH and gL (reviewed by Spear, 1993), and appears to be triggered by the binding of gD to its cognate receptors.

The human gD-binding receptors that have been identified include a member of the TNF receptor family, designated HVEM (Montgomery et al., 1996; Whitbeck et al., 1997) or herpesvirus entry protein A (HveA), and officially named TNFRSF14, and two members of the immunoglobulin superfamily (Geraghty et al., 1998; Krummenacher et al., 1998; Warner et al., 1998). The latter two proteins are related to the poliovirus receptor (CD155) (Mendelsohn et al., 1989), were originally designated poliovirus receptor-related proteins 1 (Lopez et al., 1995) and 2 (Eberlé et al., 1995), and more recently have been referred to as HveC (Geraghty et al., 1998), and HveB (Warner et al., 1998) or nectin 1 and nectin 2 (Takahashi et al., 1999), respectively. Both HveA and HveC serve as gD-binding entry receptors for wild-type HSV-1 and HSV-2 strains, whereas HveB serves as an entry receptor for only a subset of HSV strains, (Geraghty et al., 1998; Montgomery et al., 1996; Warner et al., 1998). These gD-binding cell surface receptors are expressed at different levels in various human tissues and cell lines, suggesting a specific susceptibility to HSV in certain tissues.

It has been demonstrated that heparan sulfate 3-O-sulfotransferases (3-OSTs) are present as several isoforms (i.e., 3-OST-1, 3-OST-2, 3-OST-3, 3-OST-4) that are expressed at different levels in various tissues and cells (Shworak et al., 1999). In particular, 3-OST-3 enzymes are present in two highly similar forms (3-OST-3A and 3-OST-3B). In general, different 3-OST isoforms sulfate glucosamine residues with different saccharide sequences around the modification site. For example, 3-OST-1, 3-OST-2, and 3-OST-3 generate different saccharide sequences (Liu et al., 1999a). However, the highly homologous isoforms, 3-OST-3A and 3-OST-3B, have been shown to sulfate identical saccharide sequences. The differences in sulfation of saccharide sequences are thought to correlate with differences in function. For example, heparan sulfates, which have been 3-O-sulfated by 3-OST-1, possess anticoagulant activity, however, heparan sulfates which have been 3-O-sulfated by 3-OST-2 and 3-OST-3A do not possess anticoagulant activity.

It has been shown that 3-OST-3s sulfate N-unsubstituted glucosamine residues (Liu et al., 1999b). However the majority of the glucosamine residues in HS are present either in the form of N-acetylated or N-sulfated glucosamine, and N-unsubstituted glucosamine residues are relatively rare. In fact, N-unsubstituted glucosamine residues constitute only 1–7% of total glucosamine residues (Lindahl et al., 1998). The rarity of the saccharide sequences 3-O-sulfated by the 3-OST-3s, the multiplicity of the 3-OST-3 genes in human genome, and the correlation between sulfation and function, suggest an important biological role of 3-OST-3 modified HS.

SUMMARY OF THE INVENTION

The present invention depends, in part, on the discovery that specific saccharide sequences in HS can serve as a gD-binding receptor for HSV-1 entry into cells. Thus, the present invention provides pharmaceutical preparations for inhibiting HSV-1 infection, and methods of inhibiting HSV-1 infection in a mammal using the pharmaceutical preparations of the invention.

Thus, in one aspect, the present invention provides a pharmaceutical preparation for inhibiting HSV-1 infection in a mammal, comprising a polysaccharide preparation enriched for 3-O-sulfated glucosamine residues (GlcN3S and/or GlcN3S6S). In preferred embodiments, the polysaccharide preparation is enriched for polysaccharide sequences capable of specific binding with HSV-1 gD viral glycoprotein, for example, IdoA2S-GlcN3S6S and/or IdoA2S-GlcN3S.

In another series of embodiments, the polysaccharide preparation is enriched for a polysaccharide sequence that includes the disaccharide IdoA2S-GlcNH$_2$3S6S. In preferred embodiments, the polysaccharide preparation is enriched for the trisaccharide GlcNS-IdoA2S-GlcNH$_2$3S6S, the tetrasaccharide UA2S-GlcNS-IdoA2S-GlcNH$_2$3S6S the pentasaccharide GlcNS6S-UA2S-GlcNS-IdoA2S-GlcNH$_2$3S6S, the hexasaccharide UA-GlcNS6S-UA2S-GlcNS-IdoA2S-GlcNH$_2$3S6S, heptasaccharide GlcNAc-UA-GlcNS6S-UA2S-GlcNS-IdoA2S-GlcNH$_2$3S6S, and/or the octasaccharide UA-GlcNAc-UA-GlcNS6S-UA2S-GlcNS-IdoA2S-GlcNH$_2$3S6S. In a most preferred embodiment, the polysaccharide preparation is enriched for the octasaccharide UA-GlcNAc-UA-GlcNS6S-UA2S-GlcNS-IdoA2S-GlcNH$_2$3S6S.

In one series of embodiments, the polysaccharide sequence specifically binds to HSV-1 gD with a high degree of affinity. Thus, in one embodiment, the polysaccharide preparation has a binding affinity (expressed in terms of the disassociation constant (Kd) and measured by affinity co-electrophoresis as described herein) of less than 30 μM for HSV-1 viral protein gD. In another embodiment, the polysaccharide structure has a binding specificity of less than 20 μM for HSV-1 viral protein gD. In a preferred embodiment, the polysaccharide structure has a binding specificity of less than 10 μM for HSV-1 viral protein gD. In a most preferred embodiment, the polysaccharide structure has a binding specificity of approximately 2 μM–10 μM for HSV-1 viral protein gD.

In another aspect, the present invention provides a pharmaceutical preparation for inhibiting HSV-1 infection in a mammal, including a polysaccharide that has been enriched for saccharide structures modified by a 3-OST-3 enzyme. In preferred embodiments the 3-OST-3 enzyme may be human 3-OST-3A or 3-OST-3B, or murine 3-OST-3B. Such enriched preparations may be produced by contacting a polysaccharide with a 3-OST-3 enzyme in the presence of a sulfate donor, under conditions suitable for 3-O sulfation of the polysaccharide by a 3-OST-3. In preferred embodiments, the polysaccharide preparation includes 3-O-sulfated heparan sulfate. In particularly preferred embodiments, the 3-O-sulfated heparan sulfate includes disaccharide sequences of IdoA2S-GlcN3S6S and/or IdoA2S-GlcN3S. In some embodiments the enriched preparation maybe further enriched by purification of the 3-OST-3 modified polysaccharide by a purification technique that is known in the art, for example HPLC.

In another aspect, the pharmaceutical preparations of the present invention include a pharmaceutically acceptable carrier. In preferred embodiments, the carrier may be a lotion, cream, jelly, liniment, ointment, salve, oil, foam, gel, wash, suppository, slow-releasing polymer, or coating. In other embodiments, the preparation of the present invention may include at least one skin penetrating enhancer. In preferred embodiments, the skin penetrating enhancer may be dimethylsulfoxide (DMSO), propylene glycol, isopropanol, ethanol, oleic acid, and/or N-methylpyrrolidone.

In another aspect, the present invention provides for methods of inhibiting HSV-1 infection in a mammal, using the pharmaceutical preparations of the invention.

BRIEF DESCRIPTION OF THE DRAWINGS

FIG. 1 depicts a sequence alignment of the amino acid sequences of m3-OST-3B, h3-OST-3B, and the sulfotransferase domain of h3-OST-3A (amino acids 148–406).

FIG. 2 depicts the IdoA2S-GlcNH2±6S3S substrate specificity of heparan sulfate D-glucosaminyl 3-O-sulfotrasferase (3-OST-3).

DETAILED DESCRIPTION OF THE INVENTION

DEFINITIONS

In order to more clearly and distinctly point out and describe the subject matter that applicants regard as the invention, the following definitions are provided for certain terms used in the following written description and the appended claims.

Enriched as used herein with regard to particlular polysaccharide structures within a polysaccharide preparation, the term "enriched" means that the proportion of the polysaccharide structure in a polysaccharide preparation is statistically significantly greater than the proportion of the polysaccharide structure in a naturally-occurring, untreated polysaccharide preparation. The polysaccharide preparations of the invention are enriched for 3-OST-3 sulfated polysaccharides approximately 10–100 fold. Whereas the percentage of 3-OST-3 sulfated polysaccharide in a typical unenriched preparation is less than 0.1%, the percentage of 3-OST-3 sulfated polysaccbaride in the enriched polysaccharide preparations of the invention is about 5–7%.

Heparan sulfate. As used herein, the term "heparan sulfate" or the abbreviation "HS" means a polysaccharide made up of repeated disaccharide units D-glucuronic acid or L-iduronic acid linked to N-acetyl or N-sulfated D-glucosamine. The polysaccharide is modified to a variable extent by sulfation of the 2-O-position of GlcA and IdoA residues, and the 6-O- and 3-O-positions of GlcN residues and acetylation or de-acetylation of the nitrogen of GlcN residues. Therefore, this definition encompasses all of the glycosaminoglycan compounds variously referred to as heparan(s), heparan sulfate(s), heparin(s), heparin sulfate(s), heparitin(s), heparitin sulfate(s), heparanoid(s), heparosan(s). The heparan molecules may be pure glycosaminoglycans or can be linked to other molecules, including other polymers such as proteins, and lipids, or small molecules such as biotin.

Heparan Sulfate D-Glucosaminyl 3-O-Sulfotransferases. Members of the family of 3-OSTs are responsible for the addition of sulfate groups at the 3-OH position of glucosamine in HS. These enzymes are present as several isoforms expressed from different genes at different levels in various tissues and cells, as described in WO 99/22005. The 3-OSTs act to modify HS late in its biosynthesis (reviewed by Lindahl et al., 1998) and each isoform recognizes as substrate glucosamine residues in regions of the HS chain that have specific, but different, prior modifications, including epimerization and sulfation at other nearby positions (Liu et al., 1999). Thus, different 3-OSTs generate different potential protein-binding sites in HS.

The 3-OST-3 proteins have 3-O-sulfotransferase activity on polysaccharide sequences including the sequences IdoA2S-GlcN and IdoA2S-GlcN6S, and convert these polysaccharide sequences to IdoA2S-GlcN3S or IdoA2S-GlcN3S6S, respectively. As used herein, the term "3-OST-3" is meant to include the 3-OST-3A and 3-OST-3B proteins, allelic or conservative substitution variants, and combinations thereof, and/or recombinantly produced fusions or chimeras thereof, as described in WO 99/22005.

FIG. 1 shows the sequence alignment of m3-OST-3B in comparison with the sequence of h3-OST-3B and h3-OST-3A. Single-underlined residues include the predicted membrane-spanning region of m3-OST-3B and the double-underlined residues indicate the potential sites for addition of N-linked glycans. The filled triangle marks the beginning of the conserved sulfotransferase domain. The position in this conserved domain of the amino acid substitution in h3-OST-3A (K162A) that results in loss of enzymatic activity is indicated by the shading. Within the sulfotransferase domain, m3-OST-3B is 91% identical to both human 3-OST-3s; the remaining N-terminal portion of m3-OST-3B is 81% identical to that of h3-OST-3B and unrelated to h3-OST-3A.

FIG. 2 shows the substrate specificities of two 3-OST-3 isoforms. Each enzyme isoform transfers sulfate to the 3-OH position of glucosamine residues in different disaccharide and oligosaccharide sequences. The arrows indicate the sulfated position within glucosamine by the enzyme, and the 3-O-sulfation is highlighted by rectangles. The abbreviated names for the disaccharides are listed under each chemical structure, where R represents H or $SO_3$.

Figure 1:
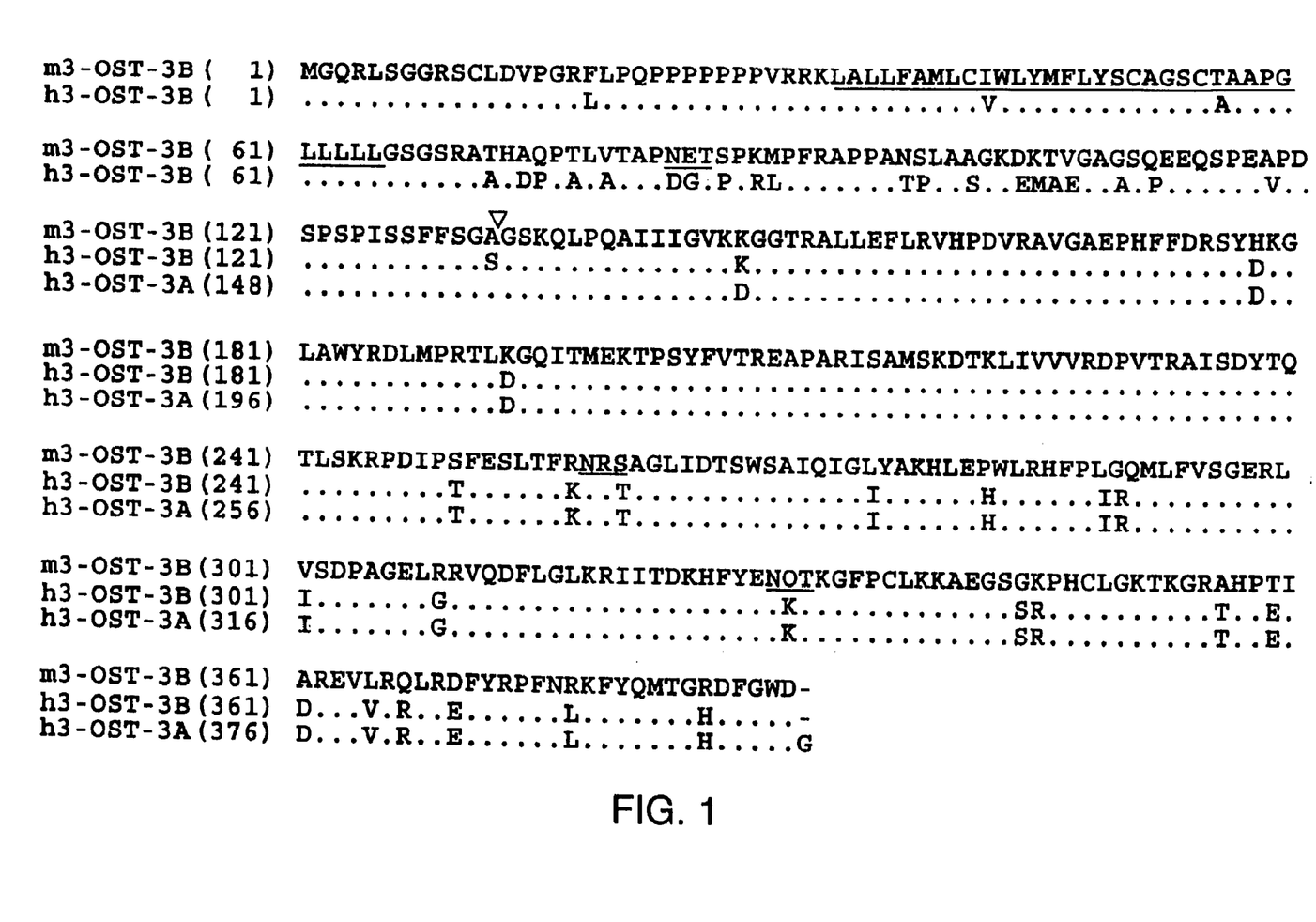
Figure 2:
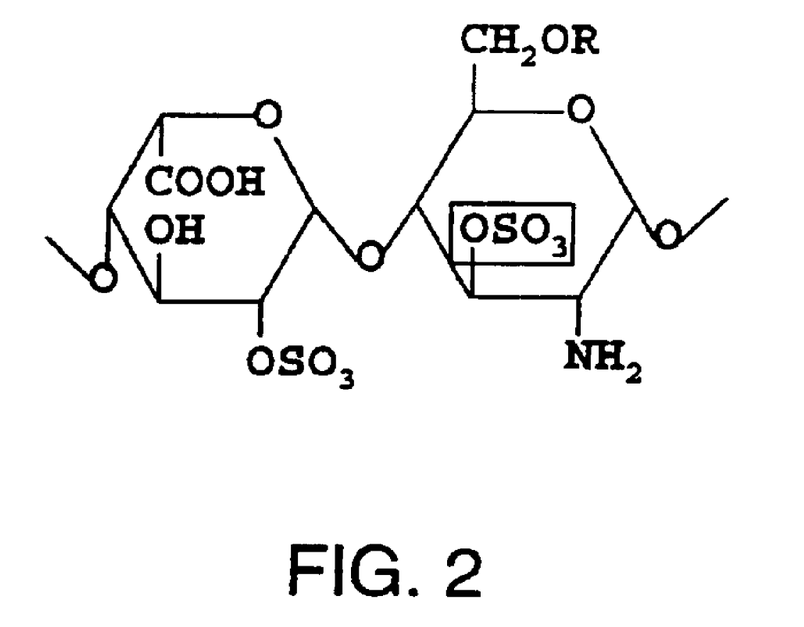

Specific Binding. As used herein, "specific binding" means that the binding affinity between a ligand and a receptor is sufficient to initiate a specific biological response. With regard to the binding of viral entry protein and target cell surface polysaccharides, the binding affinity is considered specific when the binding affinity of viral entry protein to cell surface polysaccharides is sufficient to induce fusion. With regard to the binding of viral protein gD and 3-OST-3 modified polysaccharides, binding is considered non-specific where the disassociation constant $K_d$ has a value of greater than 30 $\mu$M as measured by affinity co-electrophoresis. Furthermore, with regard to the binding of viral protein gD and 3-OST-3 modified polysaccharides, binding is considered specific where the disassociation constant $K_d$ has a value of less than 30 $\mu$M as measured by affinity co-electrophoresis.

Substantially pure. As used herein with respect to polysaccharide preparations, the term "substantially pure" means a preparation which contains at least 60% (by dry weight) the polysaccharide of interest, exclusive of the weight of other intentionally included compounds. Preferably the preparation is at least 75%, more preferably at least 90%, and most preferably at least 99%, by dry weight the polysaccharide of interest, exclusive of the weight of other intentionally included compounds. Purity can be measured by any appropriate method, e.g., column chromatography, gel electrophoresis, amino acid compositional analysis or HPLC analysis. If a preparation intentionally includes two or more different polysaccharides of the invention, a "substantially pure" preparation means a preparation in which the total dry weight of the polysaccharide of the invention is at least 60% of the total dry weight, exclusive of the weight of other intentionally included compounds. Preferably, for such preparations containing two or more polysaccharides of the invention, the total weight of the polysaccharides of the invention should be at least 75%, more preferably at least 90%, and most preferably at least 99%, of the total dry weight of the preparation, exclusive of the weight of other intentionally included compounds. Thus, if the polysaccharides of the invention are mixed with one or more other compounds (e.g., diluents, detergents, excipients, salts, sugars, lipids) for purposes of administration, stability, storage, and the like, the weight of such other compounds is ignored in the calculation of the purity of the preparation. Furthermore, when the polysaccharide is a proteoglycan, the protein component of the proteoglycan is excluded for purposes of calculating purity.

Inhibiting. As used herein with respect to viral infection, the term "inhibiting" generally refers to the ability of a pharmaceutical preparation to prevent entry of a virus in a cell. Inhibition may be measured by monitoring the expression of viral genes in cells or the number of viruses produced. The viral entry assay described herein is an example of an in vitro method of measuring viral entry, and hence, viral inhibition. As used herein with regard to both primary and recurring HSV infection, the term "inhibiting" means that the amount of virus entering a cell is decreased by a statistically significant measurable amount in a cell, culture, or organism treated with the polysaccharide preparations of the invention relative to an untreated cell, culture, or organism.

I. Role of 3-O-Sulfated HS in HSV-1 Entry

The present invention depends, in part, on the discovery that specific saccharide sequences in HS can serve as gD-binding receptors for HSV-1 entry into cells. These saccharide sequences include one of the disaccharides, -IdoA2S-GlcN3S6S- or -IdoA2S-GlcN3S-. These conclusions are based on evidence that (1) 3-OST-3s capable of introducing the final modification characteristic of these disaccharides can convert HSV-1 resistant cells to cells susceptible to HSV-1 entry, (2) the ability of the 3-OST-3s to confer susceptibility depends on the presence of the appropriate HS substrate and on enzymatic activity, (3) gD receptors are generated by the action of 3-OST3s, (4) membrane-bound and soluble gD competed with virus for the receptors generated by 3-OST-3B, and (5) HS-binding gD receptors can be removed from cells by the action of heparinases.

II. Pharmaceutical Preparations

In one aspect, the present invention provides for substantially pure pharmaceutical preparations for use in the treatment of HSV-1 infection. Such pharmaceutical preparations include a substantially pure preparation of glycosaminoglycans or proteoglycan polysaccharides, which have been enriched for saccharide sequences capable of specifically binding to the viral envelope protein gD. In a preferred embodiment, the preparation includes glycosaminoglycans or proteoglycan polysaccharides enriched for GlcN3S and/or GlcN3S6S. In a more preferred embodiment, the preparation includes glycosaminoglycans or proteoglycan polysaccharides enriched for IdoA2S-GlcN3S6S and/or IdoA2S-GlcN3S.

In another series of embodiments, the polysaccharide preparation is enriched for a polysaccharide sequence that includes the disaccharide IdoA2S-GlcNH$_2$3S6S. In preferred embodiments, the polysaccharide preparation is enriched for the trisaccharide GlcNS-IdoA2S-GlcNH$_2$3S6S, the tetrasaccharide UA2S-GlcNS-IdoA2S-GlcNH$_2$3S6S the pentasaccharide GlcNS6S-UA2S-GlcNS-IdoA2S-GlcNH$_2$3S6S, the hexasaccharide UA-GlcNS6S-UA2S-GlcNS-IdoA2S-GlcNH$_2$3S6S, heptasaccharide GlcNAc-UA-GlcNS6S-UA2S-GlcNS-IdoA2S-GlcNH$_2$3S6S, and/or the octasaccharide UA-GlcNAc-UA-GlcNS6S-UA2S-GlcNS-IdoA2S-GlcNH$_2$3S6S. In a most preferred embodiment, the polysaccharide preparation is enriched for the octasaccharide UA-GlcNAc-UA-GlcNS6S-UA2S-GlcNS-IdoA2S-GlcNH$_2$3S6S.

In preferred embodiments, the enriched polysaccharide sequence is capable of specifically binding to the viral envelope protein gD. Thus, the binding affinity between the polysaccharide sequence and the gD is sufficient to initiate a specific biological response. With regard to the binding of gD viral entry protein and the enriched polysaccharide sequences, the binding affinity is considered specific when the binding affinity of gD to the enriched polysaccharides is sufficient to induce fusion.

In particular embodiments, the binding is considered non-specific where the disassociation constant $K_d$ has a value of greater than 30 $\mu$M, as measured by affinity co-electrophoresis. Furthermore, with regard to the binding of viral protein gD and 3-OST-3 modified polysaccharides, binding is considered specific where the disassociation constant $K_d$ has a value of less than 30 $\mu$M, as measured by affinity co-electrophoresis. In one series of embodiments, the polysaccharide sequence specifically binds to HSV-1 gD with a high degree of affinity. Thus, in one embodiment, the polysaccharide preparation has a binding affinity (expressed in terms of the disassociation constant (Kd) and measured by affinity co-electrophoresis as described herein) of less than 30 $\mu$M for HSV-1 viral protein gD. In another embodiment, the polysaccharide structure has a binding specificity of less than 20 $\mu$M for HSV-1 viral protein gD. In a preferred embodiment, the polysaccharide structure has a binding specificity of less than 10 $\mu$M for HSV-1 viral protein gD. In a more preferred embodiment, the polysaccharide structure has a binding specificity of less than 5 $\mu$M for HSV-1 viral protein gD. In a most preferred embodiment, the polysaccharide structure has a binding specificity of approximately 2 $\mu$M to 10 $\mu$M for HSV-1 viral protein gD.

The enriched polysaccharide preparations of the invention may be produced by contacting a polysaccharide preparation with a 3-OST-3 enzyme, for example, 3-OST-3A and/or 3-OST-3B, in the presence of a sulfate donor under conditions that permit 3-OST-3 enzymatic activity. In particular, the 3-OST-3 proteins may be m3-OST-3B, h3-OST-3A, h3-OST-3B, allelic or conservative substitution variants, combinations thereof, and/or recombinantly produced fusions or chimeras thereof, as described in WO 99/22005. In preferred embodiments, the sulfate donor is 3'-phosphoadenosine 5'-phosphosulfate (PAPS). The enriched polysaccharide preparations of the present invention may be further enriched by one of the many purification techniques currently known in the art. For example, one of ordinary skill in the art could affinity purify the polysaccharide preparations of the invention by applying the preparation to a column or other substrate to which 3-OST-3 protein or gD has been immobilized, washing away the unbound fraction of HS, and thereafter eluting the binding fraction.

In one embodiment, the proportion of the 3-OST-3-modified residues in a polysaccharide preparation is statistically significantly greater than the proportion of the polysaccharide structure in naturally-occurring, untreated polysaccharide preparation. In a preferred embodiment, the proportion 3-OST-3-modified residues are greater than 7%.

In some embodiments, the enriched polysaccharide preparations of the present invention may be combined with one or more other compounds (e.g., diluents, detergents, excipients, stabilizers, salts, sugars, lipids, or proteins) for purposes of administration, stability, and/or storage. Thus, in some embodiments, the pharmaceutical preparations of the present invention are incorporated into conventional carriers, such as, for example, lotions, creams, jellies, liniments, ointments, salves, oils, foams, gels, washes, suppositories, slow-releasing polymers, coatings, and the like so that they can be easily applied topically in the present methods. The carriers may also include other ingredients such as, for example, pH modifiers, stabilizers, buffers, surfactants, moisturizers, colorants, thickeners, flavorings, fragrances, perfumes, and the like. The pharmaceutical preparations of the present invention may also be used with conventional birth-control or safe-sex devices. For example, the pharmaceutical preparations could be incorporated into or used in conjunction with condoms (i.e., via lubricants applied to the interior and/or exterior surfaces), diaphragms, cervical caps, or similar products. The pharmaceutical preparations of the present invention could also, for example, be introduced into a bodily orifice by hand, via suppositories, or by using conventional tampon or syringe techniques. The method of administering or delivering the pharmaceutical preparation to the potential HSV-transmission site is not critical if an effective amount of the pharmaceutical preparation is delivered to the site in a timely manner. Preferably the formulations and/or method of delivering the pharmaceutical preparations allows the pharmaceutical preparations to remain in the appropriate area during HSV-1 contact in order to maximize effectiveness.

The pharmaceutical preparations of the invention may also be combined with a skin penetrating enhancer, for example, dimethylsulfoxide (DMSO), propylene glycol, isopropanol, ethanol, oleic acid, and N-methylpyrrolidone. In preferred embodiments, the pharmaceutical preparations of the invention are combined with substance(s) that is/are appropriate for topical application to mucocutaneous tissues (i.e., tissues of the nasal, oral, vaginal, and anal orifices).

III. Methods of Treatment

In another aspect, the present invention is directed to methods of treating a mammal, (e.g., a human) diagnosed with or at risk of contracting HSV-1 infection. The present invention provides for therapeutic intervention of or prophylaxis for HSV-1 infection by reducing entry of HSV-1 into a target cell. As detailed above, 3-OST-3 modified HS binds to viral envelope protein gD and may promote the fusion of the viral coat with the target cell. Treatment or prophylaxis of HSV-1 infection may be achieved by administering a therapeutically effective amount of the pharmaceutical preparations of the invention including enriched gD-binding polysaccharide preparations to a mammal diagnosed with or at risk of HSV-1 infection. The pharmaceutical preparations of the present invention are preferably provided to a mammal directly (e.g., locally, as by injection, implantation or topical administration to a tissue locus). The preferred mode of administration of pharmaceutical preparations of the invention is topical.

In one embodiment, the pharmaceutical preparations of the invention may be used to prevent the primary (first-episode) HSV-1 infection. For example, the pharmaceutical preparation of the invention may be topically applied to tissue that is at risk of exposure to HSV-1. Thus, the present invention provides for methods of treating HSV-1 infection by administering a therapeutically effective amount of the pharmaceutical preparations of the invention to an area that may be exposed to HSV-1. In preferred embodiments, the topical administration of the pharmaceutical preparations of the present invention occurs prior to the potential exposure to HSV-1. Without being bound to any particular theory of the invention, it is contemplated that the likelihood of HSV-1 infection may be reduced by using the pharmaceutical preparations of the invention to competitively inhibit the binding of the viral envelope protein gD to 3-OST-3 modified HS on a target cell surface.

In another embodiment, the pharmaceutical preparations of the invention may be used to treat persistent (recurring) HSV-1 infection. Thus, the present invention provides for methods of treating HSV-1 infection by administering a therapeutic amount of the pharmaceutical preparations of the invention to an affected area, such as a lesion, to ameliorate the clinical manifestations of HSV-1 infection. In preferred embodiments, the topical administration of the pharmaceutical preparations of the present invention occurs at the first sign of a prodromal syndrome, a detectable subclinical manifestation (e.g., prodromal syndrome or HSV-1 shedding on mucosal surfaces detectable by PCR) and/or clinical manifestation (e.g., lesion formation) of recurrent HSV-1 infection. In most preferred embodiments, the administration of the pharmaceutical preparations of the present invention occurs at the first sign of a detectable subclinical (e.g., HSV-shedding on mucosal surfaces detected by PCR) and/or clinical manifestation (e.g., lesion formation) of recurrent HSV-1 infection and continues until the subclinical and/or clinical manifestations have subsided. Without being bound to any particular theory of the invention, it is contemplated that the frequency, intensity and/or duration of HSV-1 recurring lesions may be reduced by using the pharmaceutical preparations of the invention to competitively inhibit the binding of gD to 3-OST-3 modified HS.

IV. Materials and Methods

Cells and Viruses

Wild-type CHO cells and GAG-defective mutant cell lines (pgsA-745, a cell line that does not produce glycosaminoglycans (Esko et al., 1985); pgsD-677, a cell line that produces only chondroitin sulfate (Lidholt et al., 1992); and pgsF-17, a cell line that fails to modify the hexuronic acid residues of HS by the addition of 2-O-sulfate groups (Bai and Esko, 1996)) were grown in Ham's F12 medium supplemented with 10% fetal bovine serum. Wild-type virus strains used were HSV-1(KOS), HSV-1(Patton), HSV-1 (F) and HSV-2(333). Mutant strains included HSV-1(KOS)Rid1 and Rid2 (Dean et al., 1994). Recombinant viruses carrying the lacZ gene of *E. coli* and capable of expressing β-galactosidase as a reporter of entry included HSV-1(KOS) gL86 (Montgomery et al., 1996), HSV-1(KOS)tk12 and HSV-1(KOS)Rid1-tk12 (Warner et al., 1998).

Antibodies and Purified Recombinant Proteins

Antibodies used included rabbit antiserum R7 specific for HSV gD (Isola et al., 1989), the anti-gD mAb DL6 (Isola et al., 1989) and an anti-myc mAb (cat. no. R950-25, Invitrogen, Carlsbad, Calif.). Purified recombinant proteins included m3-OST-1 secreted from L cells (Liu et al., 1996), a secreted N-truncated form of h3-OST-3A (Liu et al. 199b) and two secreted C-truncated forms of gD-1 designated gD-1(306t) and gD-1(Δ290–299t) (Nicola et al., 1996). The h3-OST-3A, gD-1(306t), and gD-1(Δ290–299t) were produced in insect cells from baculovirus vectors and purified as described in the references cited. The hybrid protein gD-1:Fc was produced by CHO cells transfected with plasmid pBG64. The hybrid protein was harvested from the medium (Ham's F12 supplemented with 3% fetal bovine serum depleted of IgG) and the protein was purified by Protein G-Sepharose chromatography.

Screening Assay for cDNAs Encoding HSV-1 Entry Proteins

Wild-type Chinese hamster ovary (CHO) cells are resistant to HSV-1 entry (Shieh et al., 1992). A 15.5 days gestation mouse embryonic cDNA expression library (Gibco-BRL, Gaithersburg, Md.) was screened for plasmids capable of rendering transfected CHO cells susceptible to HSV-1 entry, as previously described (Montgomery et al., 1996). A single plasmid, designated pDS43, was obtained. This plasmid had an insert of 1666 base pairs, including the polyA tail with one major open reading frame encoding the protein. The sequence of the insert was deposited in GenBank (Accession No. AF168992).

Searching the protein databases using the BLAST Algorithm with the pDS43 amino acid sequence revealed that the clone has 74% identity to 3-OST-3A (Accession No. AF105376) from Residue 31 to 390 and has 86% identity to h3-OST-3B (Accession No. AF105377) from Residue 24 to 390. Such high identity to human 3-OST-3A and 3-OST-3B led to the conclusion that pDS43 encodes a murine form of 3-OST-3. The clone was shown to have 3-OST-3 activity and was therefore designated m3-OST-3B.

Transfection of the plasmids expressing 3-OST-3A and 3-OST-3B resulted in CHO-K1 becoming susceptible to KOS infection, indicating that human 3-OST-3A and 3-OST3B contain viral entry activity. However, CHO-K1 cells transfected with the plasmid expressing 3-OST-1, an isoform of 3-OST-3, remain resistant to viral infection. Transfection of the plasmid expressing 3-OST-2, which has 67% identity to m3-OST-3B from Residue 30 to 390, caused transfected CHO-K1 cells to be susceptible to viral infection.

Plasmids

Plasmid pDS43/myc-His was generated by in-frame fusion of the C-terminus of the m3-OST-3B open reading frame, through conversion of the stop codon to a BamHI site, with the myc-His tag from the plasmid pcDNA3.1/myc-His (Invitrogen, Carlsbad, Calif.). Plasmid pBG64 has the ectodomain of HSV-1(KOS) gD (amino acids 1–343) fused in frame to the Fc region of a rabbit IgG heavy chain, and cloned into pcDNA3. Plasmids described elsewhere include those expressing m3-OST-1 (Shworak et al., 1997), h3-OST-3A and h3-OST-3B (Liu et al., 1999), pBG38 expressing HveC (Geraghty et al., 1998), and pRE4 expressing HSV-1 gD (Cohen et al., 1988).

Degradation Analysis of 3-OST-3-Modified HS

Purified enzymes (m3-OST-1 or h3-OST-3A) or extracts of COS-7 cells (Shworak et al., 1997) expressing various forms of 3-OST-3 were incubated with HS prepared from wild-type CHO cells or pgsF–17 cells and [$^{35}$S]PAPS. The reaction conditions ensured the modification of all potential 3-O-sulfation sites recognized by each enzyme. In some cases the enzyme-modified or unmodified HS was then incubated with nitrous acid at pH 1.5 and 0° C. for 30 min and reduced with sodium borohydride (0.05M) under alkaline conditions at 50° C. for 30 min (Liu et al., 1999). The [$^{35}$S]disaccharides were isolated by Biogel P-2 (Indianapolis, Ind.) and analyzed on reverse phase ion pairing HPLC. The identities of the [$^{35}$S]disaccharides were determined by co-elution with [$^3$H]disaccharide standards. The disaccharides (about 60% of total loaded $^{35}$S counts)

were subfractionated on reversed-phase ion pairing HPLC with appropriate disaccharide standards.

Viral Entry Assays

Entry assays were based on quantitation of β-galactosidase expressed from the viral genome or by CHO-IE8 cells in which β-galactosidase expression is inducible by HSV infection (Montgomery et al., 1996). Cells were transiently transfected in 6-well dishes, using Lipofectamine (Gibco-BRL, Gaithersburg, Md.) with plasmids expressing one of the entry mediators or control plasmid, pcDNA3, at 1.5 to 2.0 µg per well in 1 ml. At 24 hours after transfection, the cells were replated in 96 well tissue culture dishes (2–4×10$^4$ cells/well) at least 16 hours prior to infection. Cells were washed and exposed to virus in 50 µl of phosphate-buffered saline (PBS) containing glucose and 1% calf serum (PBS-G-CS) for 6 hours at 37° C. before solubilization in 100 µl of PBS containing 0.5% NP-40 and the β-galactosidase substrate, o-nitro-phenyl β-D-galactopyranoside (ONPG, 3 mg/ml). The enzymatic activity was monitored by spectrometry at several time points after the addition of ONPG to define the interval over which the generation of product was linear with time (Dynatech ELISA reader or a Spectromax 250). Results are presented as the means of triplicate or quadruplicate determinations. Assays for inhibition of infection by soluble gD were similar, except that dilutions of virus were mixed with gD-1(Δ290–299t) or BSA and incubated for 30 minutes at 37° C. prior to addition of the mixtures (50 µl/well) to washed cell monolayers.

gD Interference Assay

Wild-type CHO cells were co-transfected, using Lipofectamine (Gibco-BRL, Gaithersburg, Md.), with m3-OST-3B expression plasmid (pDS43/myc-His) and gD expression plasmid (pRE4 for HSV-1 wild-type gD) or control plasmid (pcDNA3), in 1:4 (m3-OST-3B:gD or control) ratio, in 6-well dishes. The total amount of plasmid DNA added per well was 2.0 µg. After 24 hrs the transfected cells were replated in 96 well plates and, 24 hrs later, were exposed to various doses of β-galactosidase-expressing HSV-1. Six hours later, viral entry was quantitated as described herein.

Binding of gD-1 to 3-O-Sulfated HS

Metabolically-labeled [$^3$H]HS (2–4×10$^6$ dpm, 1.2–2.5 pmole) from wild-type CHO cells or pgsF–17 cells was incubated with [$^{35}$S]PAPS (10 µM, 20×10$^6$ dpm) and 60 ng of purified m3-OST-1 or h3-OST-3A. The average number of 3-O-sulfate groups introduced per HS molecule from wild-type CHO cells was 8 for 3-OST-1 and 14 for h3-OST-3A, based on the $^{35}$S count transferred to the HS, given the specific activities of [$^{35}$S]PAPS (18 Ci/mmole) and [$^3$H]HS (727 Ci/mmole), and assuming a molecular weight of 81,000 for HS. Each preparation of enzyme-modified or unmodified HS (1–2×10$^5$ dpm of $^3$H) was mixed with gD-1(306t) (10 βg) in 50 βl of binding buffer (50 mM Tris-HCl, pH 7.5, 150 mM NaCl and 0.01% Triton X-100) for 30 min at room temperature. The anti-gD antiserum R7 (or the anti-gD monoclonal antibody DL6) (5 µl) was added for incubation at 4° C. for 1 hr, followed by addition of Protein A-agarose gel (80 µl of 1:1 slurry) and agitation at 4° C. for an additional hour. The Protein A-agarose gel was washed with binding buffer and the bound HS eluted with 1 ml of binding buffer containing 1 M NaCl.

3-OST-3 Modified HS Binds gD with a Kd of 2 µM

Affinity co-electrophoresis (Lee et al., 1991) was performed to estimate dissociation constants for the gD-HS interactions. [$^{35}$S]HS was purified from CHO cells, modified by incubation with purified h3-OST-3A in vitro and then fractionated by co-immunoprecipitation with gD-1(306t). The fraction of HS co-precipitating with gD was designated HS$^{gDeAct}$ and the non-gD-binding fraction was designated HS$^{gDeInact}$.

Metabolically-labeled [$^{35}$S]HS was modified by incubation with purified h3-OST-3A as above except that unlabeled PAPS (10 βM) was the sulfate donor. The molecules of modified [$^{35}$S]HS capable of binding gD-1 ([$^{35}$S]HS$^{gDeAct}$) were collected by co-precipitation with gD-1 (306t) as described above. The molecules that failed to co-precipitate were designated [$^{35}$S]HS$^{gDeInact}$ although this fraction probably contained some gD-1-binding material. Purified gD-1 (306t) was cast in low melting point 1% agarose gel (Gibco-BRL, Gaithersburg, Md.) in a buffer containing 125 mM sodium acetate, 50 mM 3-(N-morpholino)-2-hydroxypropanesulfonic acid and 0.5% 3-[(3-cholamidopropyl)dimethylammonio]-1-propane-sulfonate, pH 7.0, at 9 different concentrations for [$^{35}$S]HS$^{gDeAct}$, ranging from 0 to 11 µM, and at 4 different concentrations for [$^{35}$S]HS$^{gDeInact}$, ranging from 0 to 83 µM, in each separation zone. Approximately 50,000 cpm of [$^{35}$S]HS$^{gDeAct}$ or [$^{35}$S]HS$^{gDeInact}$ was loaded in each separation zone and electrophoresis was performed at 400 mA for 2.5 hr in a cold room with circulated cold water. The gels were dried and analyzed on a Beta-scope 603 (Betagen) to determine the migration of [$^{35}$S]HS.

The [$^{35}$S]-intensity was plotted against the migration distance through the separation zone, and the migration point with the highest [$^{35}$S] intensity was defined as the migration of [$^{35}$S]HS$^{gDeAct}$. The retardation coefficient $R=(M_0-M)/M_0$, where $M_0$ is the migration of free [$^{35}$S]HS$^{gDeAct}$ and M is the observed migration of [$^{35}$S]HS$^{gDeAct}$. Provided that [$^{35}$S]HS$^{gDeAct}$ and gD-1 forms 1:1 complex and the amount of [$^{35}$S]HS$^{gDeAct}$ is far less than gD-1, a plot of $R/[gD-1]_{total}$ vs. R should yield a straight line with a slope of $-1/K_d$ according to Scatchard equation. From these data, the $K_d$ for interaction of HS$^{gDeAct}$ with gD-1(306t) was calculated to be 2 µM and the $K_d$ for HS$^{gDeInact}$ was calculated to be 43 µM or greater.

V. Experimental Results

3-OST-3-Modified HS Specifically Binds Glycoprotein gD-1

It was shown that gD binds to 3-OST-3-modified HS, but not to 3-OST-3 enzyme. HS extracted from wild-type CHO cells was unmodified or was sulfated by incubation in vitro with 3-OST-1 or h3-OST-3A, and was tested for binding to gD in co-immunoprecipitation experiments. Table 1 shows that the fraction of labeled HS bound to immunoprecipitated gD-1(306t) was enhanced almost 10-fold for HS by incubation with 3-OST-3A. Modification by 3-OST-1 did not significantly enhance the binding to gD-1(306t). After incubation with 3-OST-3A, the HS from pgsF-17 cells, a cell line that fails to modify the hexuronic acid residues of HS by the addition of 2-O-sulfite groups, bound to gD-1(306t) with about the same efficiency as unmodified HS from CHO cells.

TABLE 1

The binding of enzyme-modified HS to gD-1

| | [$^3$H]HS bound to gD-1 (306t) (%) | |
|---|---|---|
| [$^3$H]HS | Wild-type | pgsF-17 |
| Unmodified HS | 1.7 ± 0.9 (n = 5) | 0.13 ± 0.1 (n = 2) |
| 3-OST-1 modified HS[a] | 3.4 ± 1.6 (n = 2) | N.D. |
| 3-OST-3A modified HS[b] | 14.8 ± 1.7 (n = 6) | 1.6 ± 0.7 (n = 2) |

[a]The sulfated structure generated is -GlcA-GlcNS ± 6S3S-.
[b]The sulfated structure generated is -IdoA2S-GlcN ± 6S3S-.

Efforts to demonstrate direct interactions between 3-OST-3 and gD were unsuccessful. In ELISA assays no binding of purified gD-1(306t) to purified h3-OST-3A was evident, whereas binding to purified HveC was readily detected in control experiments.

3-OST-3B-Mediated Viral Entry Depends on HS Production and 2-O-Sulfation of HS

A variety of mutant cell lines defective in various aspects of GAG biosynthesis have been isolated from CHO cells (Bai and Esko, 1996; Esko, 1991). Wild-type CHO cells and several mutant cell lines were transfected with plasmids expressing myc-tagged version of m3-OST-3B or HveC, or with the empty vector, pcDNA3. The cells were then exposed to HSV-1(KOS)gL86 for quantitation of viral entry. Various cell lines transfected with the m3-OST-3B-expressing plasmid produced equivalent amounts of the protein. Mutations affecting HS biosynthesis had different consequences for HSV-1 entry, depending on whether the entry mediator was m3-OST-3B or HveC. None of the cells transfected with control plasmid was susceptible to HSV-1 entry.

Expression of m3-OST-3B resulted in HSV-1 entry only in cells capable of producing HS with the modifications characteristic of CHO cells. HSV-1 entry occurred in wild-type CHO cells and mutant cells pgsE-606, which produce HS that is under-sulfated due to the absence of one of the N-sulfotransferase isoforms (Aikawa and Esko, 1999; Bame and Esko, 1989), provided 3-OST-3 was expressed. However, HSV-1 entry did not occur in mutant lines that fail to produce HS. For example, HSV-1 entry did not occur in the following HS defective cell lines: pgsA-745, a cell line that does not produce glycosaminoglycans (Esko et al., 1985); pgsD-677, a cell line that produces only chondroitin sulfate (Lidholt et al., 1992); and pgsF-17, a cell line that fails to modify the hexuronic acid residues of HS by the addition of 2-O-sulfate groups (Bai and Esko, 1996). Because the substrate for 3-OST-3s is a glucosamine residue adjacent to 2-O-sulfated IdoA, incubation of HS from pgsF-17 cells with purified 3-OST-3A should not yield the characteristic disaccharides resulting from 3-OST-3 activity, as was confirmed experimentally.

In contrast to the results obtained for transfection with m3-OST-3B, expression of HveC rendered all the cell lines susceptible to HSV-1 entry, although the wild-type CHO cells became significantly more susceptible than any of the mutant cell lines. Binding of virus to the wild-type cells should be enhanced by interactions of gB or gC with HS as well as of gD with HveC. The ability of HS to enhance the susceptibility resulting from HveC expression depended on the level of glucosamine N-sulfation (pgsE-606 cells) and on 2-O-sulfation of hexuronic residues (pgsF-17 cells), suggesting that these groups are important for the binding of virus to cells (Feyzi et al., 1997; Herold et al., 1996).

HveC can confer greater susceptibility to HSV-1 entry than does m3-OST-3B. In the case of HveC, new gD-binding receptors are over-expressed from the transfected plasmid whereas, in the case of m3-OST-3B, the enzyme is thought to modify endogenous molecules to generate receptors for virus. Accordingly, the levels of endogenous receptor are believed to control the degree of susceptibility to infection resulting from 3-OST-3 activity.

Heparinases Removed gD-binding Receptors and Reduced Viral Entry in 3-OST-3 Cells Heparinases were shown to remove the receptors that bind gD and mediate viral entry from 3-OST-3-expressing cells. Wild-type CHO cells or pgsA-745 cells were transfected with plasmids expressing m3-OST-3B or h3-OST-3A, or with control plasmid. The transfected cells were either incubated with a mixture of heparinases I and III or in buffer without the heparinases. The cells were next incubated with a gD hybrid protein consisting of the ectodomain of gD fused to the Fc of rabbit IgG (gD-1:Fc).

Heparinase I (heparin lyase I; heparinase; EC 4.2.2.8) and heparinase III (heparitin sulfate lyase III; heparitinase, EC 4.2.2.8) were obtained from Sigma (St. Louis, Mo.). Transfected cells plated in 96-well dishes were washed twice with PBS lacking magnesium and calcium ions, overlaid with several dilutions of heparinase I and heparinase III or PBS alone, and incubated at 30° C. for 2 h. The cells were then washed with PBS and used for viral entry assays or for quantitation of gD-1:Fc binding to the cells.

Following heparinase treatment, the cells assayed for gD-binding were processed as follows. The cells were next incubated with a gD hybrid protein consisting of the ectodomain of gD fused to the Fc of rabbit IgG (gD-1:Fc). Expression of 3-OST-3A or m3-OST-3B caused enhanced binding of gD-1:Fc. In contrast, expression of 3-OST-3A or m3-OST-3B in pgs-745 cells did not enhance binding of gD-1:Fc. The enhanced binding in CHO cells was eliminated by pre-treatment of the cells with heparinases I/III.

Following heparinase treatment, the cells assayed for viral entry were processed as follows. The cells were exposed to HSV-1(KOS)gL86 at $7.5 \times 10^5$ PFU/well and viral entry was quantitated 6 hrs later. Entry into the heparinase I/III-treated cells was compared to percentage of the entry into mock-treated cells. For CHO cells expressing m3-OST-3B, treatment with heparinases I/III almost completely eliminated susceptibility to HSV-1 entry whereas, for cells expressing HveC, this treatment reduced susceptibility to HSV-1 infection by 50%.

Both Membrane Bound and Soluble gD Competes with Virus for Receptors Generated by m3-OST-3B HSV-1 entry was inhibited in CHO cells transformed with HSV-1 gD and m3-OST-3B. CHO cells were transfected with a m3-OST-3B-expressing plasmid mixed in 1:4 ratio with a gD-1-expressing plasmid or the empty vector pcDNA3. The transfected cells were then exposed to HSV-1(KOS)gL86 and viral entry quantitated after 6 hrs. Viral entry was assayed using the entry assay described herein.

HSV-1 entry was inhibited in m3-OST-3B-expressing CHO cells that were pre-incubated with soluble gD. CHO cells transfected with a plasmid expressing m3-OST-3B were exposed to HSV-1(KOS)gL86 ($7.5 \times 10^5$ PFU/well) that had been pre-incubated with gD-1($\Delta$290–299t), a soluble form of gD-1. Viral entry was assayed using the entry assay described herein.

h3-OST-3A K162 Mutant Does not Express 3-OST-3 Activity

A mutated form of h3-OST-3A, in which the Lys at position 162 was changed to Ala, was shown by Western blot analysis to be expressed at a level comparable to that of wild-type enzyme but to have little or no enzymatic activity and no viral entry activity, as described below. The 3-OST-3A mutant was transfected into COS-7 cells and the cell extract was assayed for 3-OST-3 activity. Two characteristic 3-OST-3 degradation product [$^{35}$S]disaccharides, IdoA2S-AnMan3S and IdoA2S-AnMan3S6S (corresponding to IdoA2S-GlcN3S and IdoA2S-GlcN3S6S, respectively) were absent from the [$^{35}$S]HS prepared by the cell extract transfected with 3-OST-3A mutant.

This particular amino acid substitution in a highly conserved region of the sulfotransferases was shown previously to dramatically reduce enzymatic activity of a flavonol 3-sulfotransferase with minimal effect on PAPS binding (Marsolais and Varin, 1995). Moreover, mutagenic and structural studies demonstrated that the conserved Lys has a comparable critical role in catalysis by a heparan N-sulfotransferase (Kakuta et al., 1999; Sueyoshi et al., 1998). Because the Lys 162 residue is conserved in almost all known sulfotransferase, it is likely to be a critical residue for sulfotransferase activity.

Binding of Enzyme-Modified HS to Viral Glycoproteins

The binding of enzyme-modified HS to viral glycoproteins was determined by immunoprecipitation using Protein A-agarose (Pierce, Rockford, Ill.). Briefly, enzyme-modified [$^3$H/$^{35}$S]HS (1×10$^5$ cpm of $^3$H counts) was incubated with recombinant purified HSV glycoprotein gD-1 (306t, 10 μg) (Tal-Singer et al., 1995) in 50 μl of a buffer containing 50 mM Tris, 150 mM NaCl and 0.01% Triton X-100, pH 7.5 (binding buffer) at room temperature for 30 min. Polyclonal antibody R7 (5 μl), against gD-1 (Isola et al., 1989), was added to the mixture, and the reaction was incubated at 4° C. for one additional hour. The reaction mixture was then mixed with 80 μl 1:1 slurry of pre-washed Protein A-agarose, and agitated at 4° C. for one hour or overnight. The suspended solution was centrifuged at 5,000×g for 2 min, and the supernatant was discarded. The Protein A-agarose gel was washed with 1 ml of binding buffer three times. The bound [$^3$H/$^{35}$S]HS was eluted with 1 ml of binding buffer containing 1 M NaCl.

Detection of gD-1 Receptors on Cells

CHO cells and pgsA-745 cells were transfected with pDS43 or pcDNA3 and plated in 96-well plates. Some cultures were treated with heparinases as described below prior to the assay. After washing the cells and blocking with PBS containing 3% BSA for 30 min, the cells were incubated with purified gD-1:Fc (1 μg/ml) in 1% BSA-PBS for 45 min at room temperature. The cells were then washed and fixed with 2% formaldehyde and 0.2% glutaraldehyde in PBS. Cell-bound gD-1:Fc was detected by sequential incubations with biotin-conjugated goat anti-rabbit IgG antibody (Sigma, St Louis, Mo.), Amdex™ streptavidin-horseradish peroxidase (Amersham Pharmacia Biotech, Inc., Uppsala, Sweden) and the peroxidase substrate 3,3',5,5'-tetramethyl benzidine (Sigma, St. Louis, Mo.) in 50 mM phosphate-citrate buffer. Product was quantitated by use of a Spectromax 250 ELISA (Molecular Devices Sunnyvale, Calif.) reader to measure $OD_{370}$.

REFERENCES

Aikawa, J., and Esko, J. D. (1999). Molecular cloning and expression of a third member of the heparan sulfate/heparin N-deacetylase/N-sulfotransferase family. J.Biol.Chem. 274, 2690–2695.

Bai, X., and Esko, J. D. (1996). An animal cell mutant defective in heparan sulfate hexuronic acid 2-O-sulfation. J.Biol.Chem. 271, 17711–17717.

Bame, K. J., and Esko, J. D. (1989). Undersulfated heparan sulfate in a Chinese hamster ovary cell mutant defective in heparan sulfate N-sulfotransferase. J.Biol.Chem. 264, 8059–8065.

Byrnes, A. P., and Griffin, D. E. (1998). Binding of Sindbis virus to cell surface heparan sulfate. J.Virol. 72, 7349–7356.

Chung, C. S., Hsiao, J. C., Chang, Y. S., and Chang, W. (1998). A27L protein mediates vaccinia virus interaction with cell surface heparan sulfate. J.Virol. 72, 1577–1585.

Cohen, G. H., Wilcox, W. C., Sodora, D. L., Long, D., Levin, J. Z., and Eisenberg, R. J. (1988). Expression of herpes simplex virus type 1 glycoprotein D deletion mutants in mammalian cells. J.Virol. 62, 1932–1940.

Compton, T., Nowlin, D. M., and Cooper, N. R. (1993). Initiation of human cytomegalovirus infection requires initial interaction with cell surface heparan sulfate. Virology 193, 834–841.

Corey, L., and Spear, P. G. (1988). Infections with herpes simplex viruses. N.Eng.J.Med. 314, 686–689;-749–757.

Dean, H. J., Terhune, S., Shieh, M.-T., Susmarski, N., and Spear, P. G. (1994). Single amino acid substitutions in gD of herpes simplex virus 1 confer resistance to gD-mediated interference and cause cell type-dependent alterations in infectivity. Virology 199, 67–80.

Eberlé, F., Dubreuil, P., Mattei, M. G., Devilard, E., and Lopez, M. (1995). The human PRR2 gene, related to the human poliovirus receptor gene (PVR), is the true homolog of the murine MPH gene. Gene 159, 267–272.

Esko, J. D. (1991). Genetic analysis of proteoglycan structure, function and metabolism. Curr.Opin.Cell Biol. 3, 805–816.

Esko, J. D., Stewart, T. E., and Taylor, W. H. (1985). Animal cell mutants defective in glycosaminoglycan biosynthesis. Proc.Natl.Acad.Sci.U.S.A. 82, 3197–3201.

Feyzi, E., Trybala, E., Bergstrom, T., Lindahl, U., and Spillmann, D. (1997). Structural requirement of heparan sulfate for interaction with herpes simplex virus type 1 virions and isolated glycoprotein C. J.Biol.Chem. 272, 24850–24857.

Geraghty, R. J., Krummenacher, C., Cohen, G. H., Eisenberg, R. J., and Spear, P. G. (1998). Entry of alpha herpesviruses mediated by poliovirus receptor-related protein 1 and poliovirus receptor. Science 280, 1618–1620.

Herold, B. C., Gerber, S. I., Belval, B. J., Siston, A. M., and Shulman, N. (1996). Differences in the susceptibility of herpes simplex virus types 1 and 2 to modified heparin compounds suggest serotype differences in viral entry. J.Virol. 70, 3461–3469.

Herold, B. C., Visalli, R. J., Susmarski, N., Brandt, C. R., and Spear, P. G. (1994). Glycoprotein C-independent binding of herpes simplex virus to cells requires of cell surface heparan sulphate and glycoprotein B. J.Gen.Virol. 75, 1211–1222.

Herold, B. C., WuDunn, D., Soltys, N., and Spear, P. G. (1991). Glycoprotein C of herpes simplex virus type 1 plays a principal role in the adsorption of virus to cells and in infectivity. J.Virol. 65, 1090–1098.

Isola, V. J., Eisenberg, R. J., Siebert, G. R., Heilman, C. J., Wilcox, W. C., and Cohen, G. H. (1989). Fine mapping of antigenic site II of herpes simplex virus glycoprotein D. J.Virol. 63, 2325–2334.

Jackson, T., Ellard, F. M., Ghazaleh, R. A., Brookes, S. M., Blakemore, W. E., Corteyn, A. H., Stuart, D. I., Newman, J. W., and King, A. M. (1996). Efficient infection of cells in culture by type O foot-and-mouth disease virus requires binding to cell surface heparan sulfate. J.Virol. 70, 5282–5287.

Kakuta, Y., Sueyoshi, T., Negishi, M., and Pedersen, L. C. (1999). Crystal structure of the sulfotransferase domain of human heparan sulfate N-deacetylase/N-sulfotransferase 1. J.Biol.Chem. 274, 10673–10676.

Krummenacher, C., Nicola, A. V., Whitbeck, J. C., Lou, H., Hou, W., Lambris, J. D., Geraghty, R. J., Spear, P. G., Cohen, G. H., and Eisenberg, R. J. (1998). Herpes simplex virus glycoprotein D can bind to poliovirus receptor-related protein 1 or herpesvirus entry mediator, two structurally unrelated mediators of virus entry. J.Virol. 72, 7064–7074.

Krummenacher, C., Rux, A. H., Whitbeck, J. C., Ponce de Leon, M., Lou, H., Baribaud, I., Hou, W., Zou, C., Geraghty, R. J., Spear, P. G., Eisenberg, R. J., and Cohen, G. H. (1999). The first Ig-like domain of HveC is sufficient to bind HSV gD with full affinity while the third domain is involved in oligomerization of HveC. J.Virol. in press.

Lafferty, W. E., Coombs, R. W., Benedetti, J., Critchlow, C., and Corey, L. (1987). Recurrences after oral and genital herpes simplex virus infection. Influence of site of infection and viral type. N Engl J Med 316, 1444–1449.

Lee, M. K., and Lander, A. D. (1991). Analysis of affinity and structural selectivity in the binding of proteins to glycosaminoglycans: Development of a sensitive electrophoretic approach. Proc.Natl.Acad.Sci.U.S.A. 88, 2768–2772.

Lidholt, K., Weinke, J. L., Kiser, C. S., Lugemwa, F. N., Bame, K. J., Cheifetz, S., Massagué, J., Lindahl, U., and Esko, J. D. (1992). A single mutation affects both N-acetylglucosaminyl-transferase and glucuronosyltransferase activities in a Chinese hamster ovary cell mutant defective in heparan sulfate biosynthesis. Proc.Natl.Acad.Sci.U.S.A. 89, 2267–2271.

Lindahl, U., Kusche-Gullberg, M., and Kjellén, L. (1998). Regulated diversity of heparan sulfate. J.Biol.Chem. 273, 24979–24982.

Liu, J., Shworak, N. W., Fritze, L. M. S., Edelberg, J. M., and Rosenberg, R. D. (1996). Purification of heparan sulfate D-glucosaminyl 3-O-sulfotransferase. J.Biol.Chem. 271, 27072–27082.

Liu, J., Shworak, N. W., Sinay, P., Schwartz, J. J., Zhang, L., Fritze, L. M. S., and Rosenberg, R. (1999a). Expression of heparan sulfate D-glucosaminyl 3-O-sulfotransferase isoforms reveals novel substrate specificities. J.Biol.Chem. 274, 5185–5192.

Lui, J., Shriver, Z., Blaiklock, P., Yoshida, K., Sasisekharan, R., and Rosenberg, R. D., (1999b) Heparan Sulfate D-glucoaminyl 3-O-sulfotransferase-3A sulfates N-unsubstituted glucosmine residues. J.Biol.Chem. 274, 38155–38162.

Lopez, M., Eberlé, F., Mattei, M. G., Gabert, J., Birg, F., Bardin, F., Maroc, C., and Dubreuil, P. (1995). Complementary DNA characterization and chromosomal localization of a human gene related to the poliovirus receptor-encoding gene. Gene 155, 261–265.

Marsolais, F., and Varin, L. (1995). Identification of amino acid residues critical for catalysis and cosubstrate binding in the flavonol 3-sulfotransferase. J.Biol.Chem. 270, 30458–30463.

Mauri, D. N., Ebner, R., Montgomery, R. I., Kochel, K. D., Cheung, T. C., Yu, G.-L., Ruben, S., Murphy, M., Eisenberg, R. J., Cohen, G. H., Spear, P. G., and Ware, C. F. (1998). LIGHT, a new member of the TNF superfamily, and lymphotoxin a are ligands for herpesvirus entry mediator. Immunity 8, 21–30.

Mendelsohn, C. L., Wimmer, E., and Racaniello, V. R. (1989). Cellular receptor for poliovirus: molecular cloning, nucleotide sequence, and expression of a new member of the immunoglobulin superfamily. Cell 56, 855–865.

Montgomery, R. I., Warner, M. S., Lum, B. J., and Spear, P. G. (1996). Herpes simplex virus-1 entry into cells mediated by a novel member of the TNF/NGF receptor family. Cell 87, 427–436.

Nicola, A. V., Willis, S. H., Naidoo, N. N., Eisenberg, R. J., and Cohen, G. H. (1996). Structure-function analysis of soluble forms of herpes simplex virus glycoprotein D. J.Virol. 70, 3815–3822.

Rosenberg, R. D., Shworak, N. W., Liu, J., Schwartz, J. J., and Zhang, L. (1997). Heparan sulfate proteoglycans of the cardiovascular system. J.Clin.Invest. 100, S67–S75.

Schmidt, J., Klupp, B. G., Karger, A., and Mettenleiter, T. C. (1997). Adaptability in herpesviruses: glycoprotein D-independent infectivity of pseudorabies virus. J Virol 71, 17–24.

Schroder, C., Linde, G., Fehler, F., and Keil, G. M. (1997). From essential to beneficial: glycoprotein D loses importance for replication of bovine herpesvirus 1 in cell culture. Journal of Virology 71, 25–33.

Shieh, M.-T., WuDunn, D., Montgomery, R. I., Esko, J. D., and Spear, P. G. (1992). Cell surface receptors for herpes simplex virus are heparan sulfate proteoglycans. J.Cell Biol. 116, 1273–1281.

Shworak, N. W., Liu, J., Frite, L. M. S., Schwartz J. J., Zhang, L., Logeart, D., and Rosenberg, R. D. (1997). Molecular cloning and expression of mouse and human cDNAs encoding heparan sulfate D-glucosaminyl 3-O-sulfotranserse. J.Biol.Chem. 272, 28008–28019.

Shworak, N. W., Liu, J., Petros, L. M., Zhang, L., Kobayashi, M., Copeland, N. G., Jenkins, N. A., and Rosenberg, R. D. (1999). Multiple isoforms of heparan sulfate D-glucosaminyl 3-O-sulfotransferase. J.Biol.Chem. 274, 5170–5184.

Spear, P. G. (1993). Entry of alpha herpesviruses into cells. Sem.Virol. 4, 167–180.

Sueyoshi, T., Kakuta, Y., Pedersen, L. C., Wall, F. E., Pedersen, L. G., and Negishi, M. (1998). A role of Lys614 in the sulfotransferase activity of human heparan sulfate N-deacetylase/N-sulfotransferase. FEBS Lett 433, 211–214.

Summerford, C., Bartlett, J. S., and Samulski, R. J. (1999). aVb5 integrin: a co-receptor for adeno-associated virus type 2 infection. Nature Med. 5, 78–82.

Summerford, C., and Samulski, R. J. (1998). Membrane-associated heparan sulfate proteoglycan is a receptor for adeno-associated virus type 2 virions. J.Virol. 72, 1438–1445.

Takahashi, K., Nakanishi, H., Miyahara, M., Mandai, K., Satoh, K., Satoh, A., Nishioka, H., Aoki, J., Nomoto, A., Mizoguchi, A., and Takai, Y. (1999). Nectin/PRR: an immunoglobulin-like cell adhesion molecule recruited to cadherin-based adherens junctions through interaction with afadin, a PDZ domain-containing protein. J. Cell Biol. 145, 539–549.

Tal-Singer R, Peng C, Ponce De Leon M, Abrams W R, Banfield B W, Tufaro F, Cohen G H, Eisenberg R J (1995) Interaction of herpes simplex virus glycoprotein gC with mammalian cell surface molecules. J. Virol. 69(7):4471–83.

Warner, M. S., Geraghty, R. J., Martinez, W. M., Montgomery, R. I., Whitbeck, J. C., Xu, R., Eisenberg, R. J., Cohen, G. H., and Spear, P. G. (1998). A cell surface protein with herpesvirus entry activity (HveB) confers susceptibility to infection by mutants of herpes simplex virus type 1, herpes simplex virus type 2 and pseudorabies virus. Virology 246, 179–189.

Whitbeck, J. C., Peng, C., Lou, H., Xu, R., Willis, S. H., Ponce de Leon, M., Peng, T., Nicola, A. V., Montgomery, R. I., Warner, M. S., Soulika, A. M., Spruce, L. A., Moore, W. T., Lambris, J. D., Spear, P. G., Cohen, G. H., and Eisenberg, R. J. (1997). Glycoprotein D of herpes simplex virus (HSV) binds directly to HVEM, a member of the tumor necrosis factor receptor superfamily and a mediator of HSV entry. J.Virol. 71, 6083–6093.

Willis, S. H., Rux, A. J., Peng, C., Whitbeck, J. C., Nicola, A. V., Lou, H., Hou, W., Salvador, L., Eisenberg, R. J., and Cohen, G. H. (1998). Binding kinetics of herpes simplex virus (HSV) glycoprotein D to the herpesvirus entry mediator (HVEM/HveA) using surface plasmon resonance. J.Virol. 72, 5937–5947.

What is claimed is:

1. A pharmaceutical preparation for inhibiting herpes simplex virus type-1 (HSV-1) infection in a mammal comprising a substantially pure heparan sulfate polysaccharide preparation enriched to comprise at least 5% for 3-O-sulfated glucosamine residues, wherein said substantially pure heparan sulfate polysaccharide preparation enriched for 3-O-sulfated glucosamine residues is obtained by the process comprising the step of contacting a heparan sulfate polysaccharide with a 3-OST-3 enzyme and a sulfate donor so as to produce a substantially pure heparan sulfate polysaccharide preparation enriched for 3-O-sulfated glucosamine residues.

2. The pharmaceutical preparation of claim 1, wherein said polysaccharide preparation is enriched for GlcN3S6S.

3. The pharmaceutical preparation of claim 1, wherein said 3-OST-3 enzyme is selected from the group consisting of 3-OST-3A and 3-OST-3B.

4. The pharmaceutical preparation of claim 1, wherein the preparation comprises the disaccharide sequence-IdoA2S-GlcN3S6S.

5. The pharmaceutical preparation of claim 1, wherein the preparation comprises the trisaccharide sequence GlcNS-IdoA2S-GlcNH$_2$3S6S.

6. The pharmaceutical preparation of claim 1, wherein the preparation comprises the tetrasaccharide sequence UA2S-GlcNS-IdoA2S-GlcNH$_2$3S6S.

7. The pharmaceutical preparation of claim 1, wherein the preparation comprises the pentasaccharide sequence GlcNS6S-UA2S-GlcNS-IdoA2S-GlcNH$_2$3S6S.

8. The pharmaceutical preparation of claim 1, wherein the preparation comprises the hexasaccharide sequence UA-GlcNS6S-UA2S-GlcNS-IdoA2S-GlcNH$_2$3S6S.

9. The pharmaceutical preparation of claim 1, wherein the preparation comprises the heptasaccharide sequence GlcNAc-UA-GlcNS6S-UA2S-GlcNS-IdoA2S-GlcNH$_2$3S6S.

10. The pharmaceutical preparation of claim 1, wherein the preparation comprises the octasaccharide sequence UA-GlcNAc-UA-GlcNS6S-UA2S-GlcNS-IdoA2S-GlcNH$_2$3S6S.

11. The pharmaceutical preparation of claim 1, wherein said pharmaceutical preparation comprises pharmaceutically acceptable carriers selected from the group consisting of lotions, creams, jellies, liniments, ointments, salves, oils, foams, gels, washes, suppositories, slow-releasing polymers, and coatings.

12. The pharmaceutical preparation of claim 1, wherein said pharmaceutical preparation further comprises at least one skin penetrating enhancer.

13. The pharmaceutical preparation of claim 12, wherein said skin penetrating enhancer is selected from the group consisting of dimethylsulfoxide (DMSO), propylene glycol, isopropanol, ethanol, oleic acid, and N-methylpyrrolidone.

14. A method of inhibiting herpes simplex virus type-1 (HSV-1) viral infection in mammal comprising administering to a mammal at risk of HSV-1 infection a therapeutically effective amount of a pharmaceutical composition comprising a substantially pure heparan sulfate polysaccharide preparation enriched to comprise at least 5% for 3-O-sulfated glucosamine residues, wherein said substantially pure heparan sulfate polysaccharide preparation enriched for 3-O-sulfated glucosamine residues is obtained by the process comprising the step of contacting a heparan sulfate polysaccharide with a 3-OST-3 enzyme and a sulfate donor.

15. A method of inhibiting herpes simplex virus type-1 (HSV-1) viral infection in mammal comprising administering to a mammal diagnosed with HSV-1 infection a therapeutically effective amount of a pharmaceutical composition comprising a substantially pure heparan sulfate polysaccharide preparation enriched to comprise at least 5% for 3-O-sulfated glucosamine residues, wherein said substantially pure heparan sulfate polysaccharide preparation enriched for 3-O-sulfated glucosamine residues is obtained by the process comprising the step of contacting a heparan sulfate polysaccharide with a 3-OST-3 enzyme and a sulfate donor.

16. The method of claim 14 or 15, wherein said polysaccharide preparation is enriched for structures capable of specific binding with HSV-1 gD viral glycoprotein.

17. The method of claim 14 or 15, wherein said 3-OST-3 enzyme is selected from the group consisting of 3-OST-3A and 3-OST-3B.

18. The method of claim 14 or 15, wherein said polysaccharide preparation comprises the disaccharide sequence -IdoA2S-GlcN3S6S.

19. The method of claim 14 or 15, wherein said polysaccharide preparation comprises the trisaccharide sequence GlcNS-IdoA2S-GlcNH23S6S.

20. The method of claim 14 or 15, wherein said polysaccharide preparation comprises the trisaccharide sequence UA2S-GlcNS-IdoA2S.

21. The method of claim 14 or 15, wherein said polysaccharide preparation comprises the pentasaccharide sequence GlcNS6S-UA2S-GlcNS-IdoA2S-GlcNH23S6S.

22. The method of claim 14 or 15, wherein said polysaccharide preparation comprises the hexasaccharide sequence UA-GlcNS6S-UA2S-GlcNS-IdoA2S-GlcNH23S6S.

23. The method of claim 14 or 15, wherein said polysaccharide preparation comprises the hexasaccharide sequence UA-GlcNS6S-UA2S-GlcNS-IdoA2S-GlcNH23S6S.

24. The method of claim 14 or 15, wherein said polysaccharide preparation comprises the heptasaccharide sequence GlcNAc-UA-GlcNS6S-UA2S-GlcNS-IdoA2S-GlcNH23S6S.

25. The method of claim 14 or 15, wherein said polysaccharide preparation comprises the octasaccharide sequence UA-GlcNAc-UA-GlcNS6S-UA2S-GlcNS-IdoA2SGlcNH23S6S.

26. The method of claim 14 or 15, wherein said pharmaceutical preparation comprises pharmaceutically acceptable carrier selected from the group consisting of lotions, creams, jellies, liniments, ointments, salves, oils, foams, gels, washes, suppositories, slow-releasing polymers, and coatings.

27. The method of claim 14 or 15, wherein said pharmaceutical preparation further comprises at least one skin penetrating enhancer.

28. The method of claim 14 or 15, wherein said skin penetrating enhancer is selected from the group consisting of dimethylsulfoxide (DMSO), propylene glycol, isopropanol, ethanol, oleic acid, and N-methylpyrrolidone.

* * * * *